United States Patent [19]

Effland et al.

[11] 4,053,599
[45] Oct. 11, 1977

[54] PIPERAZIONALKYLPYRROLOBENZOXA-ZALKANES

[75] Inventors: Richard C. Effland, Bridgewater; Larry Davis, Flemington, both of N.J.; Wolfgang Schaub, Kelkheim, Germany

[73] Assignee: American Hoechst Corporation, Bridgewater, N.J.

[21] Appl. No.: 661,534

[22] Filed: Feb. 26, 1976

[51] Int. Cl.² .................. A61K 31/495; C07D 295/10
[52] U.S. Cl. ............................ 424/250; 260/268 TR; 260/268 H; 260/326.5 J; 260/326.9
[58] Field of Search ................. 260/268 TR; 424/250

[56] References Cited

U.S. PATENT DOCUMENTS

| 3,751,415 | 8/1973 | Schmutz et al. ............. 260/268 TR |
| 3,884,920 | 5/1975 | Schmutz et al. ............. 260/268 TR |

*Primary Examiner*—Paul M. Coughlan, Jr.
*Attorney, Agent, or Firm*—Curtis, Morris & Safford

[57] ABSTRACT

Novel piperazinoalkylpyrrolobenzoxazalkanes, physiologically tolerable acid addition salts thereof and a method of preparing same are described. These compounds are useful as antihypertensive agents.

17 Claims, 1 Drawing Figure

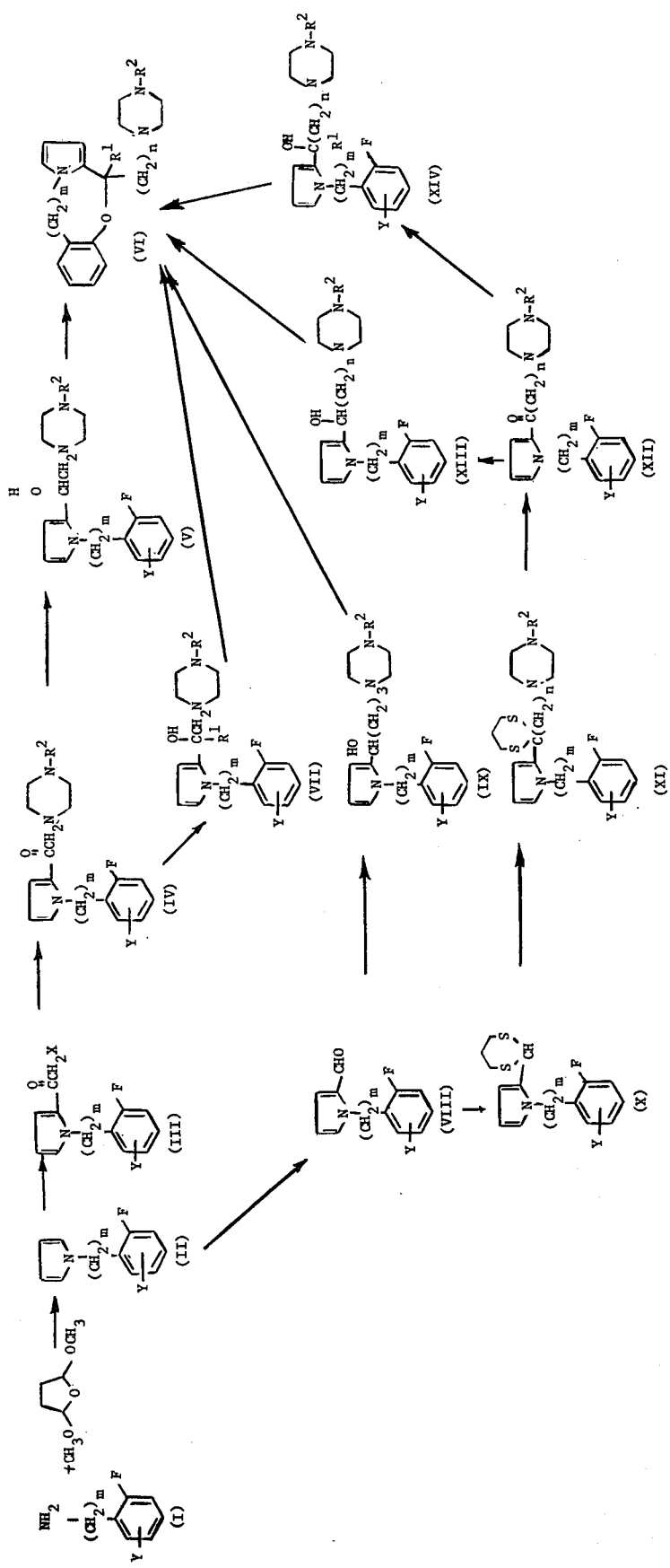

PIPERAZIONALKYLPYRROLOBENZOXAZALKANES

This invention relates to novel piperazinoalkylpyrrolobenzoxazalkanes and to their physiologically tolerable acid addition salts which are useful as antihypertensive agents, to methods of treatment with pharmaceutically effective amounts thereof and to pharmaceutical compositions containing such compounds as essential active ingredients.

To the best of our knowledge, the compounds of this invention have not heretofore been described or suggested. The compounds herein disclosed represent a new tricyclic ring structure and display significant pharmacological activity as antihypertensives.

The compounds of the present invention conform to the formula

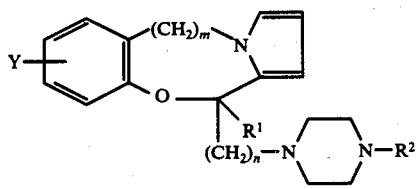

wherein Y is hydrogen, halogen, lower alkoxy, lower alkyl, trifluoromethyl, nitro or amino; $R^1$ is hydrogen or lower alkyl; $R^2$ is lower alkyl, phenyl, halophenyl, lower alkoxyphenyl, lower alkylphenyl, trifluoromethylphenyl or nitrophenyl; $m$ is the integer 1 or 2 and $n$ is 1, 2 or 3; and the acid addition salts thereof. In the above definitions, halogen means chlorine, iodine, fluorine and bromine and lower alkyl and lower alkoxy mean those radicals of from 1 to 4 carbon atoms.

Preferred embodiments of the invention are those compounds wherein $R^1$ is hydrogen. More preferred embodiments are those compounds wherein $R^2$ is phenyl, halophenyl, lower alkoxyphenyl, or lower alkylphenyl. Optimum compounds are those in which $R^2$ is phenyl.

Acids useful for preparing the acid addition salts of the invention include inorganic acids such as hydrochloric, hydrobromic, sulfuric, nitric, phosphoric and perchloric acids, as well as organic acids such as tartaric, citric, acetic, succinic, maleic, fumaric, oxalic and malonic acids.

The compounds of the present invention are prepared by the several methods of preparation which are outlined below and illustrated in the attached flow sheet. When mentioned below or in the flow sheet, $n$, $m$, $R^1$, $R^2$ and Y are, with exceptions noted, as defined earlier and X is chlorine or bromine.

METHOD A

1. An orthofluorophenylalkylamine (I) is reacted with 2,5-dimethoxytetrahydrofuran to produce an orthofluorophenylalkylpyrrole (II).

Compounds of formula (I) wherein $m$ is 1 can be obtained by brominating a 2-fluorotoluene to produce a 2-fluorobenzylbromide; reacting the 2-fluorobenzylbromide with potassium phthalimide by a Gabriel's synthesis to form a corresponding N-benzylphthalimide and cleaving the phthalimide by thermal addition of hydrazine to for a 2-fluorobenzylamine of formula (I).

Compounds of formula (I) wherein $m$ is 2 can be obtained by chlorinating a 2-fluorotoluene to produce a 2-fluorobenzylchloride reacting the benzyl chloride with sodium cyanide to form a corresponding benzyl cyanide and reducing the cyano radical with diborane to produce a 2-fluorophenethylamine of formula (I).

2. An orthofluorophenylalkylpyrrole is allowed to react with a halogenated acetonitrile such as chloroacetonitrile in the presence of an organic solvent which is inert under the reaction conditions at a cooled temperature preferably 0°–5°, and the reaction solution is saturated with hydrogen chloride gas to form the corresponding ketimine. The ketimine is subjected to hydrolysis to form the corresponding haloketone (III). A preferred organic solvent for carrying out the reaction is ether.

3. A haloketone is reacted with an N-substituted piperazine of the formula

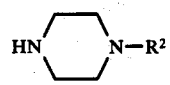

according to the method described by Teotino et al. in U.S. Pat. No. 3,706,750 to form a corresponding pyrrylpiperazinoketone (IV).

4. A pyrrlpiperazinoketone is reduced to its corresponding pyrrylpiperazino ethanol (V) by a method known to the art such as the method described by Teotino et al. in U.S. Pat. No. 3,539,589. A preferred method utilizes sodium borohydride as the reducing agent and carrying out the reduction in isopropyl alcohol at a temperature of from ambient to the reflux point of the reaction solution.

5. The reaction of a pyrrylpiperazino ethanol with a suitable base produces a tricyclic compound of the present invention (VI) wherein $R^1$ is hydrogen and $n$ is 1. A preferred method utilizes sodium hydride as the base in the presence of an organic solvent such as dry benzene or dimethylformamide.

METHOD B

1. A pyrrylpiperazinoketone (IV) is reacted with a Grignard reagent of the formula $R^1MgX$ under Grignard conditions and then the reaction mixture is hydrolyzed with ice-water to give a corresponding pyrrylpiperazino alkanol (VII) wherein $R^1$ is alkyl. Refluxing ether is preferred as the reaction medium in such Grignard reactions.

2. A pyrrylpiperazino alkanol is treated by the procedure described above in Method A, step 5, to produce a corresponding tricyclic compound of the present invention (VI) wherein $R^1$ is alkyl and $n$ is 1.

METHOD C

1. An aldehyde (VIII) is prepared from the orthofluorophenylalkylpyrrole by a method known to the art. One such method is the Vilsmeier-Haack Reaction described in Chem. Ber. 60, 119 (1927).

2. The aldehyde is reacted with a Grignard reagent of the formula

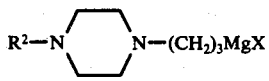

by a method known to the art to produce a corresponding pyrrylpiperazinobutanol (IX). A preferred method is carrying out the reaction in a combined solvent of ether and benzene at a temperature of 45° C.

3. The pyrrylpiperazinobutanol is treated by the procedure described above in Method A, step 5, to produce a corresponding tricyclic compound of the present invention (VI), wherein n is the integer 3.

METHOD D

1. An aldehyde (VIII) in an organic solvent such as chloroform is reacted with 1,3-propanedithiol at about ambient temperature to produce a dithiane (X). The yield and purity of the dithiane is enhanced by addition of hydrogen chloride gas to the reaction mixture at −15° C.

2. The dithiane is dissolved in an organic solvent such as tetrahydrofuran and the solution cooled to about between −80° and −20° C and reacted with n-butyllithium. The reaction mixture is maintained at about between −80° and −20° C. and a substituted piperazinoalkyl halide of the formula

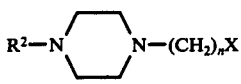

wherein n is the integer 2 or 3 and the reaction mixture is allowed to react at about between −20° C. and ambient temperature to produce a pyrrylpiperazinodithiane (XI).

3. A pyrrylpiperazinodithiane is treated with mercuric chloride and acetonitrile in the presence of an acid scavenger such as calcium carbonate and water to produce a corresponding pyrrylpiperazinoketone (XII).

4. The pyrrylpiperazinoketone (XII) is reduced by the procedure described above in Method A, step 4, to a pyrrylpiperazinoalkanol (XIII) wherein n is the integer 2 or 3 which is treated by the procedure described above in Method A, step 5 to produce a corresponding tricyclic compound of the present invention (VI) wherein n is the integer 2 or 3.

METHOD E

1. A pyrrylpiperazinoketone (XII) is treated by the procedure described above in Method B, step 1, to a corresponding pyrrylpiperazinoalkanol (XIV) wherein $R^1$ is alkyl and n is 2 or 3.

2. An above pyrrylpiperazinoalkanol is treated by the procedure described above in Method A, step 5, to produce a corresponding tricyclic compound of the present invention (VI) wherein $R^1$ is alkyl and n is 2 or 3.

The compounds of the present invention are useful antihypertensive agents due to their ability to depress blood pressure in mammals. Antihypertensive activity is measured in the spontaneous hypertensive rat by the indirect tail cuff method described by A. Schwartz, Ed., *Methods in Pharmacology*, Vol. I, page 135, Appleton-Century-Crofts, New York, New York 1971. In this procedure a group of 5 animals is treated orally with the drug for 3 days in relation to a control group of the same number. The drop in blood pressure is measured on the 3rd day following administration. For example the antihypertensive activity, expressed as mm Hg decrease in mean arterial blood pressure in this test, of 4-(4-phenylpiperazinomethyl)-4H, 10H-pyrrolo[2,1-c][1,4]benzoxazepine and 10,11-dihydro-4-(4-phenylpiperazinomethyl)-4H-pyrrolo[2,1-c][1,4]benzoxazocine is −49.6 mm Hg at a dose of 100 mg/kg and −47.33 mm Hg at a dose of 50 mg/kg, respectively. The above data illustrates that the compounds of the present invention are useful for the treatment of hypertension when administered to mammals at doses of from 0.1 to 100 mg/kg of body weight.

Further examples of compounds of the invention are:
4-(4-butylpiperazinomethyl)-4H, 10H-pyrrolo[2,1-c][1,4]benzoxazepine;

8-amino-4-[4-(4-fluorophenyl)piperazinomethyl]-4H, 10H-pyrrolo[2,1-c][1,4]benzoxazepine;

10,11-dihydro-6-methyl-4-ethyl-[(4-ethylpiperazino)methyl]-4H-pyrrolo[2,1-c][1,4]benzoxazocine;

4-[4-(2-nitrophenyl)piperazinomethyl]-4H, 10H-pyrrolo[2,1-c]-[1,4]benzoxazepine;

4-methyl-[4-(3-trifluoromethylphenyl)piperazinoethyl]-4H,-10H-pyrrolo[2,1-c][1,4]benzoxazepine;

7-bromo-4[4-(4-nitrophenyl)piperazinopropyl]-4H, 10H-pyrrolo-[2,1-c][1,4]benzoxazepine;

4-butyl-4-(4-phenylpiperazinopropyl)-4H, 10H-pyrrolo[2,1-c]-[1,4]benzoxazepine;

7-methoxy-4-(4-phenylpiperazinomethyl)-4H, 10H-pyrrolo-[2,1-c][1,4]benzoxazepine;

6-nitro-4-(4-phenylpiperazinopropyl)-4H, 10H-pyrrolo[2,1-c]-[1,4]benzoxazepine; and 10,11-dihydro-4-(phenylpiperazinoethyl)-6-trifluoromethyl-4H-pyrrolo[2,1-c][1,4]benzoxazocine.

The compounds of the present invention may be administered to a patient by a convenient route such as orally, intramuscularly, intraveneously, subcutaneously or intraperitoneally. The preferred route of administration is oral, for example, with an inert diluent or with an edible carrier or in gelatin capsules or tablets.

For the purpose of oral therapeutic administration, the active compounds of this invention may be incorporated with excipients and used in the form of tablets, troches, capsules, elixirs, suspensions, syrups, wafers, chewing gum, and the like. These preparations should contain at least 0.5% of active compound, but may be varied depending upon the particular form and may conveniently be between 7% to about 70% by weight of the unit. The amount of active compound in such compositions is such that a suitable dosage will be obtained. Preferred compositions and preparations according to the present invention are prepared so that an oral dosage unit form contains between 1 and 200 milligrams of active compound.

Tablets, pills, capsules, troches, and the like may also contain the following ingredients: a binder such as gum tragacanth or gelatin; an excipient such as starch or lactose, a disintegrating agent such as alginic acid, potato starch and the like; a lubricant such as magnesium stearate; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain various other materials which modify the physical form of the dosage unit, for example, coatings. Thus, tablets or pills may be coated with sugar, shellac, or both. A syrup may contain, in addition to the active compounds, sucrose as a sweetening agent, preservatives, colorings, materials and flavors. Materials used in preparing these various compositions must be pharmaceutically pure and non-toxic in the amounts utilized.

For the purpose of parenteral therapeutic administration, the active compounds of the invention may be incorporated into a solution or suspension. These preparations should contain at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The present invention is further illustrated by the following examples.

EXAMPLE 1 a. A solution of 40 g of 1-(2-fluorobenzyl)pyrrole and 17.2 g of chloroacetonitrile in 200 ml of anhydrous ether at a temperature between 0 and $-5°$ C is saturated with hydrogen chloride gas and then the solution is stirred until a heavy white cake forms. This cake is broken up and permitted to sit for one hour at ambient temperature. The white solid is filtered, washed with ether and dried and then hydrolyzed in water and extracted with ether. Concentration of the ether extracts leaves white crystals, mp 76°-78° C, of 2-chloroacetyl-1-(2-fluorobenzyl)pyrrole.

b. A mixture of 10.1 g of 2-chloroacetyl-1-(2-fluorobenzyl)pyrrole, 6.5 g of N-phenylpiperazine and 4.1 g of triethylamine in 40 ml of methanol is stirred at ambient temperature for 24 hours. A precipitate forms which is collected, washed with methanol and dried leaving a white solid which is recrystallized from methanol to give the product, mp 91°-93° C., of 1-(2-fluorobenzyl)-2-[α-(4-phenylpiperazino)acetyl]pyrrole.

c. A mixture of 5 g of 1-(2-fluorobenzyl)-2-[α-(4-phenylpiperazino)-acetyl]pyrrole and 1 g of sodium borohydride in 55 ml of isopropyl alcohol is refluxed for 20 hours. The isopropyl alcohol is removed leaving a white solid which is stirred with water for 30 minutes and extracted into ether. The ether extracts are dried and the ether removed leaving a colorless oil which solidifies upon standing to a white solid, mp 94-96° C., of 1-[1-(2-fluorobenzyl)-2-pyrryl]-2-(4-phenylpiperazino)ethanol.

d. A solution of 9.0 g of 1-[1-(2-fluorobenzyl)-2-pyrryl[-2-(4phenylpiperazino)ethanol in 20 ml of dimethylformamide is added portionwise at ambient temperature to a suspension of 1.11 g sodium hydride in 20 ml of dimethylformamide. The reaction mixture is allowed to stand at ambient temperature for 1 hour and at 70° C for 6 additional hours and then stirred at ambient temperature for 3 more hours. The mixture is poured into ice-water and extracted with benzene. The combined benzene extracts are washed with water and dried and the benzene removed leaving a colorless oil. The addition of an ethanol-ether mixture to the oil produces a solid product which is collected by filtration and washed with ether to leave a white solid, mp 138°-140° C., of 4-(4-phenylpiperazinomethyl)-4H, 10H-pyrrolo[2,1-c][1,4]benzoxazepine.

Analysis: Calculated for $C_{23}H_{25}N_3O$: 76.84%C; 7.03%H; 11.69%N. Found: 76.71%C; 7.01%H; 11.75%N.

EXAMPLE 2 a. A mixture of 17.6 g of 2-chloroacetyl-1-(2-fluorobenzyl)pyrrole, Example 1a, 13.8 g of 1-(4-chlorophenyl)-piperazine and 7.1 g of triethylamine in 70 ml of methanol is stirred at ambient temperature for 29 hours. A white solid forms which is collected, washed with methanol and dried leaving a product, mp 116-117° C., of 2-{α-[4-(4-chlorophenyl)piperazino]-acetyl}-1-(2-fluorobenzyl)-pyrrole.

b. To a suspension of 3.35 g of sodium borohydride in 150 ml of isopropyl alcohol is added 18.2 g of 2-{α-[4-(4-chlorophenyl)piperazino]acetyl}-1-(2-fluorobenzyl)-pyrrole and then an additional 50 ml of isopropyl alcohol. The reaction mixture is refluxed for 24 hours and the isopropyl alcohol removed under vacuum and the residue is stirred with water for 1 hour and extracted into chloroform. The chloroform is removed leaving a white solid which is recrystallized from absolute ethanol to give the product, mp 113°-114°C., of 2-[(4-chlorophenyl)- piperazino]-1-[1-(2-fluorobenzyl)-2-pyrry]ethanol.

c. A solution of 9.2 g of a 2-[(4-chlorophenyl)piperazino]-1-[1-(2-fluorobenzyl)-2-pyrrl]ethanol in 25 ml of warm dimethylformamide is added portionwise to a stirred suspension of 1.05 g of sodium hydride in 20 ml of dimethylformamide. The reaction mixture is stirred at ambient temperature for 1 hour and then at 70°C for 5 additional hours. The mixture is allowed to cool to ambient temperature and poured into an ice-water mixture and extracted into benzene. The combined benzene extracts are washed successively with water and a saturated sodium chloride solution and dried. The benzene is removed leaving a solid which is recrystallized from isopropyl alcohol producing the white solid, mp 150°-151°C, of 4-[4-(4-chlorophenyl)piperazinomethyl]-4H, 10H-pyrrolo[2,1-c][1.4]benzoxazepine.

Analysis: Calculated for $C_{23}H_{24}ClN_3O$: 70.12%C; 6.15%H; 10.67%N. Found: 70.14%C; 6.19%H; 10.69%N.

EXAMPLE 3 a. Samples of 2-chloroacetyl-1-(2-fluorobenzyl)pyrrole and 2-methoxyphenylpiperazine are treated by the procedure described in example 2a to give the white solid, mp 99°-101°C, of 1-(2-fluorobenzyl)-2-{α-[4-(2-methoxyphenyl)piperazino]acetyl}pyrrole.

b. A mixture of 18.5 g of 1-(2-fluorobenzyl)-2-{α-[4-(2-methoxyphenyl)piperazino]acetyl}pyrrole and 3.4 g of sodium borohydride in 200 ml of isopropanol is refluxed for 20 hours. The isopropanol is removal leaving a white solid which is stirred with water for 30 minutes and extracted into ether. The combined ether extracts are dried and the ether removed leaving a white solid which is triturated with ethanol and filtered to produce the white solid, mp 108°-111° C, of 1--[1-(2-fluorobenzyl)-2-pyrryl]-2-[4-(2-methoxyphenyl)piperazino]ethanol.

c. A solution of 11.5 g of 1-[1-(2-fluorobenzyl)-2pyrryl]-2-[4-(2-methoxyphenyl)piperazino]ethanol in 30 ml of dimethylformamide is added portionwise to a suspension of 1.32 g of sodium hydride in 20 ml of dimethylformamide. After total addition the reaction mixture under nitrogen is stirred at ambient temperature for 1 hour and at 70°C for 6 additional hours and then allowed to cool to ambient temperature. The reaction is poured into an ice-water mixture and extracted into benzene. The combined benzene extracts are washed successively with water and a saturated sodium chloride solution and dried and the benzene removed leaving an oil. The oil is dissolved in acetonitrile and filtered then stirred with charcoal and refiltered through celite. The acetonitrile is removed leaving a faintly pink oil which crystallizes as a white solid upon standing. The solid is triturated with hexane and filtered and then recrystallized from isopropanol leaving the white solid, mp 95°–97° C, of 4-[4-(2-methoxyphenyl)piperazinomethyl]-4H, 10H-pyrrolo[2,1-c][1,4]benzoxazepine.

Analysis: Calculated for $C_{24}H_{27}N_3O_2$: 73.99%C; 7.00%H; 10.79%N. Found: 73.82%C; 7.06%H; 10.82%N.

EXAMPLE 4 a. A mixture of 20.1 g of 2-chloroacetyl-1-(2-fluorobenzyl)pyrrole, example 1a, 14.1 g of 2-tolylpiperazine and 8.1 g of triethylamine in 80 ml of methanol is stirred at ambient temperature for 40 hours. The methanol is removed leaving an orange semi-solid which is treated with water and extracted into chloroform. The combined extracts are dried and the chloroform evaporated under vacuum leaving an orange oil. The oil is dissolved in ether, the ether solution filtered and the solution acidified with ethereal-hydrogen chloride leaving the hydrochloride salt as a crystalline precipate which is recrystallized from an isopropanol-methanol mixture to give the light tan solid, mp 184°–185° C, of 1-(2-fluorobenzyl)-2-{2-[4-(2-tolyl)-piperazino]acetyl}pyrrole hydrochloride.

b. A solution of 20.0 g of 1-(2-fluorobenzyl)-2-{2-[4-(2-tolyl)-piperazino]acetyl}pyrrole, free base of a, in 160 ml of isopropyl alcohol is added portionwise to a suspension of 3.9 g of sodium borohydride in 160 ml of isopropyl alcohol. The reaction mixture is refluxed for 24 hours and the solvent removed leaving a semi-solid which solidifies upon treatment with water. The solid is recrystallized from an ethyl acetate-cyclohexane mixture to give white crystals, mp 95.5°–97.5°C, of 1-[1-(2-fluorobenzyl)-2-pyrryl]-2-[4f-(2-tolyl)[piperazino]ethanol.

c. A solution of 4.0 g of 1-[1-(2-fluorobenzyl)-2-pyrryl]-2-[4-(2-tolyl)piperazino]ethanol in 10 ml of dimethylformamide is added under nitrogen a stirred suspension of 0.6 g of sodium hydride in 10 ml of dimethylformamide. The reaction mixture is stirred at ambient temperature for 1 hour and then at 70° C for an additional 5 hours. The mixture is allowed to cool to ambient temperature and is poured onto an ice-water mixture to produce a very viscous product. The product is extracted into ether, washed with water and dried. The ether is removed leaving a light brown oil which is redissolved in ether. The ether solution is filtered and acidified with ethereal-malonic acid forming the malonate salt as a white precipate. The salt is recrystallized from an ethyl acetate-methanol mixture to produce the slightly reddish solid, mp 140° C, dec., of 4-[4-(2-tolyl)-piperazino]methyl-4H, 10H-pyrrolo[2,1-c][1,4]benzoxazepine malonate.

Analysis: Calculated for $C_{24}H_{27}N_3O$ $C_3H_4O_4$: 67.91%C; 6.54%H; 8.80%N. Found: 67.96%C; 6.61%H; 8.70%N.

EXAMPLE 5 a. 2- fluorophenethylpyrrole is treated with chloroacetonitrile according to an analagous procedure described above in Example 1a to produce 2-chloroacetyl-1-(2-fluorophenethyl)pyrrole.

b. To a solution of 30.0 g of 2-chloroacetyl-1-(2-fluorophenethyl)-pyrrole and 11.3 g of triethylamine in 100 ml of methanol is added dropwise a solution of 18.3 g of 4-phenylpiperazine in 30 ml of methanol. After total addition the reaction mixture is stirred at ambient temperature for 3 hours at reflux for an additional 2 hours and allowed to stand at ambient temperature for 16 hours. The methanol is removed leaving a brown semi-solid. The semi-solid is dissolved in chloroform and the chloroform solution is washed with water, dried and filtered and the chloroform removed leaving a brown oil which solidified upon standing to a tan solid. The solid is converted to its hydrochloride salt which is recrystallized from an ethyl acetate-methanol mixture to leave the product, mp 185° C, dec., of 1-(2-fluorophenethyl)-2-[α-(4-phenylpiperazino)acetyl]pyrrole hydrochloride c. A solution of 20.0 g of 1-(2-fluorophenethyl)-2-[α-(4-phenylpiperazino) acetyl]pyrrole, free base of b, in 150 ml of isopropyl alcohol is added dropwise to a suspension of 3.8 g of sodium borohydride in 100 ml of isopropyl alcohol. After total addition the reaction mixture is stirred at 80° C for 20 hours, allowed to cool and filtered and the isopropyl alcohol removed leaving a white semi-solid which is treated with water and extracted into chloroform. The chloroform solution is washed with water, dried and filtered and the chloroform removed leaving a white solid which is recrystallized from n-hexane to leave the product, mp 116°–120° C., of 1-[1-(2-fluorophenethyl)-2-pyrryl]-2-(4-phenylpiperazino)-ethanol.

d. A solution of 6.2 g of 1-[1-(2-fluorophenethyl)-2-pyrryl]-2-(4-phenylpiperazino)ethanol in 50 ml of dimethylformamide is added dropwise to a suspension of 625 mg of sodium hydride in 50 ml of benzene. After total addition the reaction mixture is maintained at 85° C for 5 hours, allowed to cool and then poured onto an ice-water mixture. The bi-phasic mixture is stirred for 30 minutes and extracted with ether. The combined ether extracts are washed with water and dried and filtered and the solvent removed leaving a dark oil. The oil is purified by elution on a dry silica gel column with ethyl acetate to yield a solid material. The solid is recrystallized twice from petroleum ether to yield the product, mp 87°–90° C, of 10,11-dihydro-4-(4-phenylpiperazinomethyl)-4H-pyrrolo[2,1-c]-[1,4]-benzoxazocine.

Analysis: Calculated for $C_{24}H_{27}N_3O$: 77.18% C; 7.29% H; 11.25% N. Found: 76.87% C 7.36%H; 11.27%N.

EXAMPLE 6 a. A solution of (4-chloro-2-fluorobenzyl)pyrrole and chloroacetonitrile in ether is treated by the procedure described in Example 1a to produce 2-chloroacetyl-1-(4-chloro-2-fluorobenzyl)pyrrole.

b. A mixture of 2-chloroacetyl-1-(4-chloro-2-fluorobenzyl)pyrrole, N-phenylpiperazine and triethylamine in methanol is treated by the procedure described in Example 1b to produce 1-(4-chloro-2-fluorobenzyl)-2-[α-(4-phenylpiperazino)acetyl]pyrrole.

c. The reduction and treatment of 1-(4-chloro-2-fluorobenzyl)-2-[α-(4-phenylpiperazino)acetyl]pyrrole by the procedure described in Example 1c produces 1-[1-(4-chloro-2-fluorobenzyl)-2-pyrryl[-2-(4-phenylpiperazino)ethanol.

d. The condensation and treatment of 1-[1-(4-chloro-2-fluorobenzyl)-2-pyrryl[-2-(4-phenylpiperazino)ethanol by the procedure described in Example 1d produces 7-chloro-4-(4-phenylpiperazinomethyl)-4H, 10H-pyrrolo[2, 1-c][1,4]benzoxazepine.

EXAMPLE 7 a. A solution of 1-(2-fluorobenzyl)-2-[α-4-phenylpiperazine)acetyl]-pyrrole, example 1b, in ether is added dropwise to a stirring solution of an appropriate amount of n-propylmagnesium bromide prepared from magnesium turnings and n-propylbromide. The mixture is refluxed for 4 hours, allowed to cool, hydrolyzed with ice-water and treated with concentrated ammonium chloride solution to dissolve the magnesium hydroxide precipitate. The organic phase is separated and the aqueous phase extracted with ether and the organic phases are combined, washed with a 5% sodium bicarbonate solution and water and dried. Removal of the ether leaves 2-[1-(2-fluorobenzyl)-2-pyrryl]-2-hydroxy-1-(4-phenylpiperazino)pentane.

b. The condensation and treatment of 2-[1-(2-fluorobenzyl)-2-pyrryl]-2-hydroxy-1-(4-phenylpiperazino)pentane by the procedure described above in example 1d produces 4-(n-propyl)-4-(4-phenylpiperazinomethyl)-4H, 10H-pyrrolo[2,1-c][1,4]benzoxazepine.

EXAMPLE 8 a. In a 500 ml three neck round bottom flask 8 g of dimethylformamide is cooled to 5°C and 16.9 g of phosphorous oxychloride is added dropwise with stirring while maintaining the temperature below 20°C. After total addition the mixture is stirred at ambient temperature for 15 minutes, 25 ml of ethylene dichloride introduced and the solution cooled to 5°C. The temperature of the solution is maintained at this low temperature with stirring during the addition of a solution of 17.5 g of 1-(2-fluorobenzyl)pyrrole, in 25 ml of ethylene dichloride. The reaction solution is stirred at this temperature for 30 minutes at ambient temperature for an additional 30 minutes and then refluxed under nitrogen for 5 hours. The mixture is allowed to cool to ambient temperature and a solution of 75 g of sodium acetate trihydrate in 120 ml of water is added. The two phase mixture is stirred vigorously at ambient temperature for 15 minutes and then refluxed for 30 minutes. After the reaction mixture cools to ambient temperature the ethylene dichloride layer is removed and the aqueous phase is extracted with ether. The combined organic extracts are washed twice with water and a saturated sodium chloride solution and dried. Removal of the solvent leaves a light yellow oil which solidifies upon standing to a pale yellow solid which is recrystallized from an ether-hexane mixture to give nearly white crystals, mp 39°-41° C, of 1-(2-fluorobenzyl)pyrrole-2-carboxaldehyde.

b. The Grignard reagent of 4-phenylpiperaznopropylmagnesium bromide is added to benzane and the mixture is refluxed at 45°C for 1 hour. The mixture is permitted to cool and a solution of 1-(2-fluorobenzyl)pyrrole-2-carboxaldehyde in ether is added and then the mixture is stirred at 45°C for 20 hours. The reaction is permitted to cool, poured into ammonium chloride solution and the ammonium chloride solution is stirred for 30 minutes and extracted with chloroform. The combined chloroform extracts are washed well with water, dried and filtered and the solvent removed leaving 1-[1-(2-fluorobenxyl)-2-pyrryl]-4-(4-phenylpiperazino)butanol.

c. The condensation and treatment of 1-[1-(2-fluorobenzyl)-2-pyrryl[-4-(4-phenylpiperazino)butanol by the procedure described above in example 1d produces 4-[3-(4-phenylpiperazino)propyl[-4H, 10H-pyrrolo[2,1-c][1,4]-benzoxazepine.

EXAMPLE 9 a. A solution of 25.0 g of 1-(2-fluorobenzyl)pyrrole-2-carboxaldehyde, example 8a, and 13.5 g of 1,3-propanedithiol in 200 ml of chloroform is stirred at ambient temperature for 1 hour and the mixture is cooled to $-15°C$. Hydrogen chloride gas is bubbled into the mixture over a 10 minute span and after stirring the reaction mixture for 20 hours at ambient temperature the mixture is washed successively with water, 10% potassium hydroxide solution, and water and dried. After filtering the solvent is evaporated leaving a yellow solid which is recrystallized twice from hexane to give an off-white solid, mp 105°-106°C, of 2-[1-(2-fluorobenzl)-2-pyrryl]-1,3-dithiane.

b. To a solution of 25.0 g of 2-[1-(2-fluorobenzyl)-2-pyrryl]-1,3dithiane in 150 ml tetrahydrofuran at $-60°$ C is added portionwise a solution of 50 ml of n-butyllithium in hexane over a 30 minute span. After stirring at $-20°$ C for 1 hour, the mixture is cooled to $-60°$ C, and 12.4 g of 4-phenylpiperazinoethyl chloride is added portionwise over a five minute span. The reaction mixture is stirred at $-20°$ C for six hours and allowed to stand for 14 hours at 5° C and then stirred at ambient temperature for 4 additional hours. The mixture is filtered and the solvent evaporated off leaving a dark oil, which is converted to an oxalate salt. The salt is reconverted to the free base and purified on a silica gel column eluted with chloroform to give the base as a solid which is recrystallized from hexane to give the solid, mp $\sim 55°$ C, of 2-(4-phenylpiperazinoethyl)-2-[1-(2-fluorobenzyl)-2-pyrryl]-1,3-dithiane. Infrared and nuclear magnetic resonance spectra confirm this structure.

c. To a solution of mercuric chloride and calcium carbonate in aqueous 80% acetonitrile is added a solution of 2-(4-phenylpiperazinoethyl)-2[1-(2-fluorobenzl)-2-pyrryl]-1,3-dithiane in aqueous 80% acetonitrile. The reaction mixture is stirred at reflux for 4 hours and then the mixture is permitted to cool and filtered through celite. The filter cake is washed with a hexane-dichloromethane mixture and the organic phase is washed successively with a 5M aqueous ammonium acetate solution and water, dried and filtered and the solvent evaporated off to give 2-[3-(4-phenyl)-piperazinopropionyl]-1-(2-fluorobenzl)pyrrole.

d. The reduction of 2-[3-(4-phenyl)piperazinopropionyl]-1-(2-fluorobenzyl)pyrrole by the procedure described in Example 1c produces 1-[1-(2-fluorobenzyl)-2-pyrryl]-2-[3-(4-phenyl)piperazino]-1-propanol.

e. The condensation and treatment of 1-[1-(2-fluorobenzyl)-2-pyrryl]-2-[3-(4-phenyl)piperazino]-1-propanol by the procedure described in Example 1d produces 4-(4-phenyl)piperazinoethyl)-4H, 10H, -pyrrolo[2,1-c]-[1,4]benzoxazepine.

EXAMPLE 10 a. A sample of 1-(2-fluorobenzyl)-2-[2-(4-phenyl-piperazino)-propionyl]pyrrole is alkylated with the Grignard reagent, ethylmagnesium bromide and then hydrolyzed by the procedure described above in Example 7b to produce 1-[1-(2-fluorobenzyl)-2-pyrryl]-2-pyrryl]-2-[(3-hydroxy)-4-phenylpiperazino)]pentane.

b. The condesation and treatment of 1-[1-(2-fluorobenzyl)-2-pyrryl]-2-[3-hydroxy)-(4-phenyl-piperazino)]pentane by the procedure described above in Example 1d produces 4-ethyl-4-(4-phenylpiperazino-ethyl)-4-H, 10H-pyrrolo-[2,1-c][1,4]benzoxazepine.

EXAMPLE 11 a. A mixture of 2-chloroacetyl-1-(2-fluorobenzl)pyrrole, Example 1a, N-methylpiperazine and triethylamine in methaol is treated by the procedure described in Example 1b to produce 1-(2-fluorobenzyl)-2[α-(4-methylpiperazino)-acetyl]pyrrole.

b. The 1-(2-fluorobenzyl)-2-[2-(4-methylpiperazino)-acetyl]pyrrole is subjected to reduction and condensation by the procedures described above in Examples 1c and d, respectively, to produce 4-(4-methylphenylpiperazinometyl)-4H, 10H-pyrrolo[2,1-c][1,4]benzoxazepine.

We claim:
1. A compound of the formula

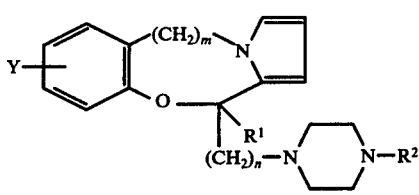

wherein Y is hydrogen, halogen, lower alkoxy, lower alkyl, trifluoromethyl, nitro or amino; $R^1$ is hydrogen or lower alkyl; $R^2$ is lower alkyl, phenyl, halophenyl, lower alkoxyphenyl, lower alkylphenyl, trifluoromethylphenyl or nitrophenyl; m is the integer 1 or 2 and n is the integer 1, 2 or 3; and the physiologically tolerable acid addition salts thereof.

2. A compound as defined in claim 1 wherein Y is hydrogen or halogen and $R^2$ is phenyl, halophenyl, methoxyphenyl or methyphenyl.

3. A compound as defined in claim 2 wherein Y and $R^1$ are hydrogen and m and n are both 1.

4. A compound as defined in claim 2 wherein Y and $R^1$ are hydrogen; m is 1 and n is 2.

5. A compound as defined in claim 2 wherein Y and $R^1$ are hydrogen; m is 1 and n is 3.

6. A compound as defined in claim 2 wherein Y is hydrogen; $R^1$ is hydrogen, m is 2 and n is 1.

7. A compound defined in claim 1 wherein $R^2$ is lower alkyl

8. The compound as defined in claim 1 which is 4-(4-phenylpiperazinomethyl)-4H, 10H, -pyrrolo[2,1-c][1,4]benzoxazepine.

9. The compound defined in claim 1 which is 10, 11-dihydro-4-(4-phenylpiperazinomethyl)-4H, 10H-pyrrolo[2,1-c][1,4benzoxazocine.

10. A method of treating hypertension which comprises administering to a patient a pharmaceutically effective amount of a compound defined in claim 1.

11. A pharmaceutical composition which comprises between about 0.5 and about 70 percent by weight of a compound defined in claim 1 as an essential active ingredient, the balance being a pharmaceutically acceptable carrier therefor.

12. A process for the preparation of a piperazinoalkyl-pyrrolobenzoxazalkane of the formula

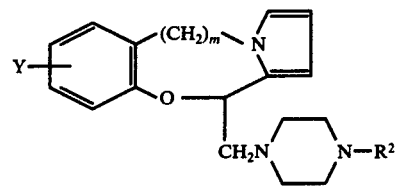

wherein Y, $R^2$ and m are as defined in claim 1; which comprises reacting an orthofluorophenylalkylpyrrole of the formula

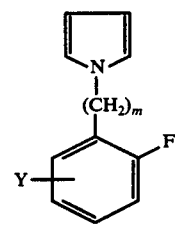

with a halogenated acetonitrile in the presence of an organic solvent which in inert under the reaction conditions at a cooled temperature and introducing hydrogen chloride gas into the reaction solution forming a ketimine; hydrolyzing said ketimine to produce a haloketone of the formula

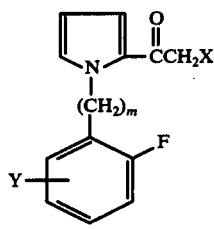

wherein X is chlorine or bromine; reacting said haloketone with an N-substituted piperazine of the formula

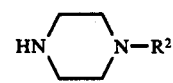

at a temperature of about ambient in the presence of an acid scavenger to produce a pyrrylpiperazino ketone of the formula

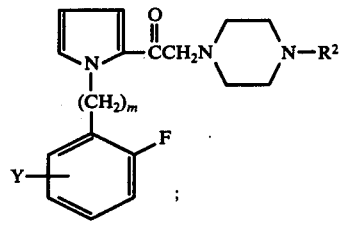

;

reducing said pyrrylpiperazino ketone to a pyrrlypiperazino ethanol of the formula

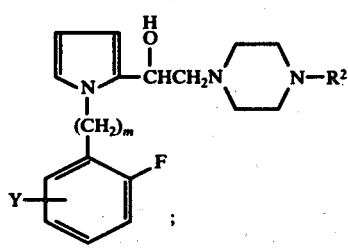

and reacting said pyrrlpiperazino ethanol with a mineral base to effect condensation to said piperazinoalkylpyrrolobenzoxazalkane.

13. The process according to claim 12 wherein the mineral base effecting condensation of said pyrrylpiperazino ethanol is sodium hydride.

14. A process for the preparation of a piperazinoalkylpyrrolobenzoxazalkane of the formula

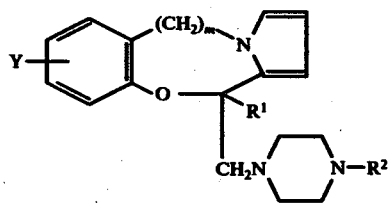

wherein Y, $R^2$ and m is as defined in claim 1 and $R^1$ is lower alkyl which comprises reacting a pyrrlaminoketone of the formula

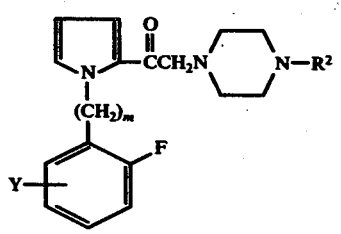

with a Grignard reagent of the formula $R^1MgX$ wherein X is bromine or chlorine under Grignard conditions; hydrolyzing the reaction mixture to form a pyrrylpiperazino alkanol of the formula

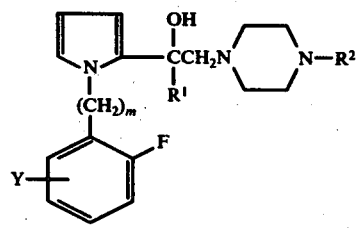

and reacting said pyrrylpiperazino alkanol with a mineral base to effect condensation to said piperazinoalkylpyrrolobenzoxazalkane.

15. A process for the preparation of a piperazinoalkylpyrrolobenzoxazalkane of the formula

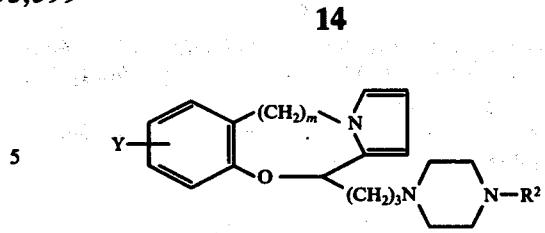

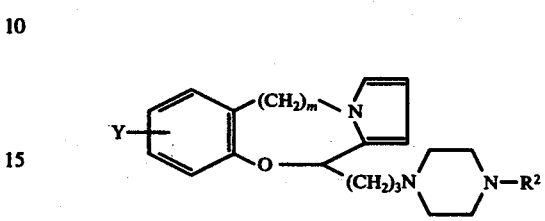

wherein Y, $R^2$ and m are as defined in claim 1 which comprises reacting an orthoflurophenylalkylpyrrole of the formula

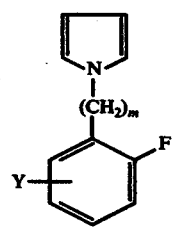

with dimethylformamide in the presence of a dehydrating agent and an organic solvent at a reaction temperature of from about 0°C to ambient to form an aldehyde of the formula

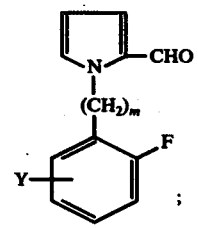

reacting said aldehyde with a Grignard reagent of the formula

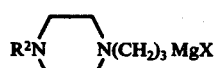

wherein X is bromime or chlorine to form a pyrrylpiperazino butanol of the formula

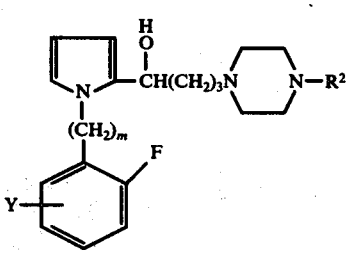

and reacting said pyrrylpiperazino butanol with a mineral base to effect condensation to said piperazinoalkyl-pyrrolobenzoxazalkane.

16. A process for the preparation of a piperazinoalkyl-pyrrolobenzoxazalkane of the formula

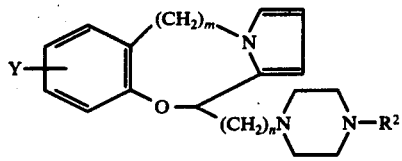

wherein Y, R², m and n are as defined in claim 1 which comprises reacting an aldehyde of the formula

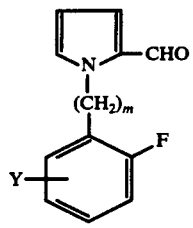

with 1,3-propanedinol in an organic solvent at about ambient temperature to form a dithiane of the formula

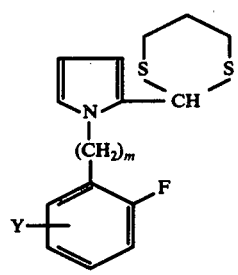

converting said dithiane to a pyrrylpiperazino dithiane of the formula

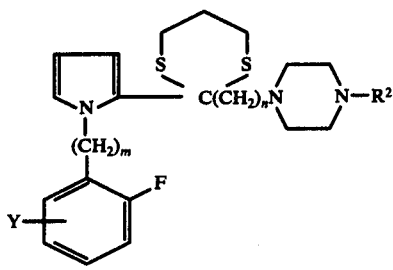

by reacting said dithiane with n-butyl lithium to form a lithio intermediate and reacting said lithio intermediate in situ with a piperazinoalkyl halide of the formula

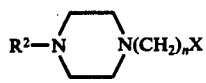

wherein X is bromine or chlorine reacting said pyrrylaminodithiane with mercuric chloride in aqueous acetonitrile in the presence of an acid scavenger to form a pyrrylpiperazino ketone of the formula

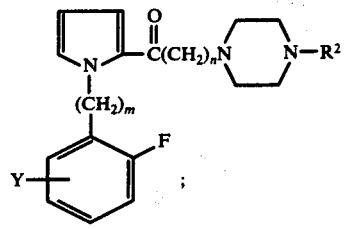

reducing said pyrrylpiperazino ketone to a pyrrylpiperazino alkanol of the formula

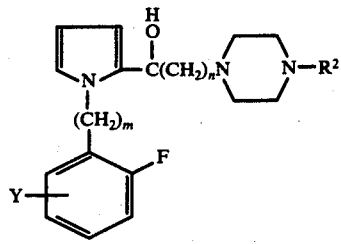

and reacting said pyrrylpiperazino alkanol with a mineral base to effect condensation to said piperazinoalkyl-pyrrolobenzoxazalkane.

17. A process for the preparation of a piperazinoalkyl-pyrrolobenzoxazalkane of the formula

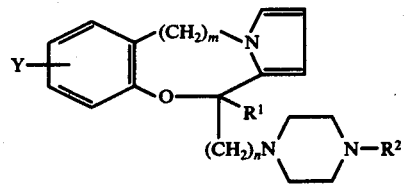

wherein Y, R² and m are as defined in claim 1 and n is the integer 2 or 3 which comprises reacting a pyrrylpiperazno ketone of the formula

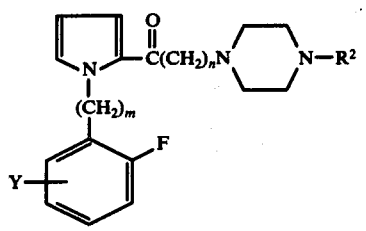

with a Grignard reagent of the formula R¹MgX under Grignard conditions; hydrolyzing the reaction mixture to form a pyrrylpiperazino alkanol of the formula

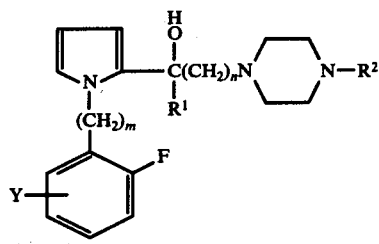

and reacting said pyrrylpiperazino alkanol with a mineral base to effect condensation to said piperazinopyrrolobenzoxazalkane.

* * * * *

UNITED STATES PATENT AND TRADEMARK OFFICE
CERTIFICATE OF CORRECTION

PATENT NO. : 4,053,599

DATED : October 11, 1977

INVENTOR(S) : Effland et al.

It is certified that error appears in the above-identified patent and that said Letters Patent are hereby corrected as shown below:

In the Heading, Item [54], "PIPERAZION..." should be --PIPERAZINO...--;

Column 1, line 66, "for" should be --form--;

Column 4, line 16, "...-4H,-10H-..." should be --...-4H,10H-...--;

line 20, "...[2,1-c]-[1,4]..." should be --...[2,1-c][1,4]...--;

Column 5, line 46, "...piperazino)-acetyl]..." should be --...piperazino)acetyl]...--;

lines 55 to 56, "...pyrryl[-2-(4phenyl..." should be --...pyrryl]-2-(4-phenyl...--;

Column 6, line 15, "...benzyl)-pyrrole" should be --...benzyl)pyrrole--;

line 26, "...phenyl)- piperazino]..." should be --...phenyl)piperazino]...--;

lines 26 to 27, "...pyrry]ethanol" should be --...pyrryl]ethanol--;

line 28, "...phenyl)" should be --...phenyl)- --;

UNITED STATES PATENT AND TRADEMARK OFFICE
CERTIFICATE OF CORRECTION

PATENT NO. : 4,053,599
DATED : October 11, 1977
INVENTOR(S) : Effland et al.

It is certified that error appears in the above-identified patent and that said Letters Patent are hereby corrected as shown below:

Column 6, line 29, "...pyrrl]ethanol" should be --...pyrryl]ethanol--;

line 64, "...-2pyr-" should be --...-2-pyr- --;

Column 7, line 37, "...tolyl)-piperazino]..." should be --...tolyl)piperazino]...--;

line 46, "...[4f-(2-tolyl)[piperazino]..." should be --...[4-(2-tolyl)piperazino]...--;

line 66, "$C_{24}H_{27}N_3O \quad C_3H_4O_4$" should be --$C_{24}H_{27}N_3O \cdot C_3H_4O_4$--;

Column 8, line 8, "...ethyl)-pyrrole" should be --...ethyl)pyrrole--;

line 18, "solidified" should be --solidifies--;

line 38, "...piperazino)-ethanol" should be --...piperazino)ethanol--;

line 53, "...[2,1-c]-[1,4]..." should be --...[2,1-c][1,4]...--;

UNITED STATES PATENT AND TRADEMARK OFFICE
CERTIFICATE OF CORRECTION

PATENT NO. : 4,053,599
DATED : October 11, 1977
INVENTOR(S) : Effland et al.

It is certified that error appears in the above-identified patent and that said Letters Patent are hereby corrected as shown below:

Column 9, line 4, "...pyrryl[-2-(4-..." should be

--...pyrryl]-2-(4-...--;

line 7, "...pyrryl[-2-(4-..." should be

--...pyrryl]-2-(4-...--;

line 14, "...acetyl]-pyrrole" should be

--...acetyl]pyrrole--;

Column 10, line 6, "...benxyl)-..." should be --...benzyl)- --;

line 9, "...pyrryl[-4-..." should be

--...pyrryl]-4-...--;

line 11, "...propyl[-4H,   10H-..." should be

--...propyl]-4H,10H-...--;

line 28, "...benzl)-2-..." shold be --...benzyl)-2-...-- line 30, "...-1,3dithiane" should be

--...-1,3-dithiane--;

line 49, "...benzl)-2-..." should be

--...benzyl)-2-...--;

UNITED STATES PATENT AND TRADEMARK OFFICE
CERTIFICATE OF CORRECTION

PATENT NO. : 4,053,599
DATED : October 11, 1977
INVENTOR(S) : Effland et al.

It is certified that error appears in the above-identified patent and that said Letters Patent are hereby corrected as shown below:

Column 10, line 59, "...benzl)pyrrole" should be

--...benzyl)pyrrole--;

line 67, "...[2,1-c]-[1,4]..." should be

--...[2,1-c][1,4]...--;

Column 11, line 4, "...piperazino)-propionyl]..." should be

--...piperazino)propionyl]...--;

lines 7 to 8, delete the second set of -- -2-pyrryl]--;

line 8, "...-4-phenyl..." should be

--...-(4-phenyl...--;

line 13, "...-4-H,10H-..." should be --...-4H,10H-...--;

line 16, "...benzl)pyrrole" should be

--...benzyl)pyrrole--;

line 19, "...-2[α-(4-..." should be --...-2-[α-(4-...--;

line 20, "...piperazino)-acetyl]..." should be

--...piperazino)acetyl]...--;

line 25, "...metyl)..." should be --...methyl)...--;

UNITED STATES PATENT AND TRADEMARK OFFICE
CERTIFICATE OF CORRECTION

PATENT NO. : 4,053,599
DATED : October 11, 1977
INVENTOR(S) : Effland et al.

It is certified that error appears in the above-identified patent and that said Letters Patent are hereby corrected as shown below:

Claim 8, line 59, "...-4H,   10H,   -pyrrolo..." should be --...-4H,10H-pyrrolo...--;

Column 13, lines 1 to 2, "...pyrrlypiper..." should be --...pyrrylpiper...--;

line 15, "pyrrlpiperazino" should be --pyrrylpiperazino--

Column 12, line 31, "...which in inert..." should be --...which is inert...--;

Claim 14, line 35, "pyrrlamino..." should be --pyrrylamino...--;

Claim 15, line 15, delete second formula appearing before "wherein Y, $R^2$ and m...";

line 20, "...orthofluro..." should be --...orthofluoro...--;

Claim 17, line 40, "piperazno" should be --piperazino--;

UNITED STATES PATENT AND TRADEMARK OFFICE
CERTIFICATE OF CORRECTION

PATENT NO. : 4,053,599

DATED : October 11, 1977

INVENTOR(S) : Effland et al.

It is certified that error appears in the above-identified patent and that said Letters Patent are hereby corrected as shown below:

In the Flow Chart, in Formula (IX),

"...$\overset{HO}{C}H(CH_2)_3N$..." should be --...$\overset{\overset{OH}{|}}{C}H(CH_2)_3N$...--.

Signed and Sealed this

Thirtieth Day of May 1978

[SEAL]

Attest:

RUTH C. MASON  
Attesting Officer

LUTRELLE F. PARKER  
Acting Commissioner of Patents and Trademarks

UNITED STATES PATENT OFFICE
CERTIFICATE OF CORRECTION

Patent No. 4,053,599            Dated October 11, 1977

Inventor(s) Richard C. Effland et al.

It is certified that error appears in the above-identified patent and that said Letters Patent are hereby corrected as shown below:

Claim 16, line 28, "1,3-propanedinol" should read -- 1,3-propanedithiol --.

Signed and Sealed this

Fifteenth Day of August 1978

[SEAL]

Attest:

RUTH C. MASON  
Attesting Officer

DONALD W. BANNER  
Commissioner of Patents and Trademarks